United States Patent
Daly et al.

(10) Patent No.: US 9,119,676 B2
(45) Date of Patent: Sep. 1, 2015

(54) BONE SCREW FIXATION

(71) Applicant: DePuy Synthes Products, Inc., Raynham, MA (US)

(72) Inventors: Erin Daly, Nashua, NH (US); Charles M. Bartish, Jr., Raynham, MA (US); Jonathan Fanger, Raynham, MA (US); SeungKyu Daniel Kwak, Shanghai (CN); Andrew E. Medeiros, Fall River, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 109 days.

(21) Appl. No.: 13/723,991

(22) Filed: Dec. 21, 2012

(65) Prior Publication Data

US 2013/0338715 A1    Dec. 19, 2013

Related U.S. Application Data

(62) Division of application No. 11/867,771, filed on Oct. 5, 2007, now Pat. No. 8,361,130.

(60) Provisional application No. 60/828,428, filed on Oct. 6, 2006.

(51) Int. Cl.
*A61B 17/70* (2006.01)
*A61B 17/86* (2006.01)

(52) U.S. Cl.
CPC ......... *A61B 17/7053* (2013.01); *A61B 17/7032* (2013.01); *A61B 17/7037* (2013.01);
(Continued)

(58) Field of Classification Search
CPC .... A61B 17/84; A61B 17/844; A61B 17/863; A61B 17/8685; A61B 17/70; A61B 17/7001; A61B 17/7032; A61B 17/7034; A61B 17/7035; A61B 17/7037; A61B 17/7038; A61B 17/704; A61B 17/7041; A61B 17/7046
USPC ............ 606/60, 246–279, 300–320, 325–328
See application file for complete search history.

(56) References Cited

U.S. PATENT DOCUMENTS

| 867,429 A | 10/1907 | Simmerman |
| 1,091,674 A | 3/1914 | Lee |

(Continued)

FOREIGN PATENT DOCUMENTS

| EP | 1348390 A2 | 10/2003 |
| WO | 9416634 A1 | 8/1994 |
| WO | 0067653 A1 | 11/2000 |

OTHER PUBLICATIONS

Suk, et al., "Unilateral Versus Bilateral Pedicle Screw Fixation in Lumbar Spinal Fusion", SPINE, vol. 25, No. 14, pp. 1843-1847, 2000.

(Continued)

*Primary Examiner* — Eduardo C Robert
*Assistant Examiner* — Lynnsy Summit
(74) *Attorney, Agent, or Firm* — Nutter McClennen & Fish LLP

(57) ABSTRACT

Various methods and devices are provided for bone screw fixation. In one exemplary embodiment, the methods and devices provide a bone fixation device that includes a receiving head having a recess adapted to seat a spinal rod therein and a shank extending distally from the receiving head. An anti-rotation mechanism can be located distal of a distal end of the receiving head and around a proximal portion of the shank, and it can be configured to interact with bone to prevent rotation of at least a portion of the bone fixation device relative to the bone.

6 Claims, 20 Drawing Sheets

(52) U.S. Cl.
CPC ........... *A61B17/7044* (2013.01); *A61B 17/864* (2013.01); *A61B 17/7038* (2013.01); *A61B 2017/8655* (2013.01)

(56) References Cited

U.S. PATENT DOCUMENTS

| | | | |
|---|---|---|---|
| 1,784,026 A | 12/1930 | Olson | |
| 1,845,428 A | 2/1932 | Llewellyn | |
| 2,077,804 A | 4/1937 | Morrison | |
| 2,685,877 A | 8/1954 | Dobelle | |
| 3,016,077 A | 1/1962 | Yocum | |
| 3,247,752 A * | 4/1966 | Greenleaf et al. | 411/542 |
| 3,711,347 A * | 1/1973 | Wagner et al. | 156/91 |
| 3,953,140 A | 4/1976 | Carlstrom | |
| 4,041,939 A * | 8/1977 | Hall | 606/254 |
| 4,579,491 A | 4/1986 | Kull | |
| 4,636,121 A | 1/1987 | Miller | |
| 4,716,893 A | 1/1988 | Fischer et al. | |
| 4,760,843 A | 8/1988 | Fischer et al. | |
| 4,790,304 A | 12/1988 | Rosenberg | |
| 4,871,289 A | 10/1989 | Choiniere | |
| 4,943,292 A | 7/1990 | Foux | |
| 4,988,351 A * | 1/1991 | Paulos et al. | 606/232 |
| 5,053,036 A | 10/1991 | Perren et al. | |
| 5,057,111 A | 10/1991 | Park | |
| 5,098,434 A * | 3/1992 | Serbousek | 606/308 |
| 5,127,912 A * | 7/1992 | Ray et al. | 606/250 |
| 5,127,914 A | 7/1992 | Calderale et al. | |
| 5,151,103 A | 9/1992 | Tepic et al. | |
| 5,176,682 A | 1/1993 | Chow | |
| 5,209,753 A | 5/1993 | Biedermann et al. | |
| 5,269,784 A * | 12/1993 | Mast | 606/288 |
| 5,364,399 A | 11/1994 | Lowery et al. | |
| 5,366,455 A * | 11/1994 | Dove et al. | 606/250 |
| 5,368,593 A * | 11/1994 | Stark | 606/308 |
| 5,472,452 A | 12/1995 | Trott | |
| 5,474,553 A | 12/1995 | Baumgart et al. | |
| 5,478,342 A | 12/1995 | Kohrs | |
| 5,489,210 A | 2/1996 | Hanosh | |
| 5,501,684 A | 3/1996 | Schlapfer et al. | |
| 5,520,690 A | 5/1996 | Errico et al. | |
| 5,534,027 A | 7/1996 | Hodorek | |
| 5,578,034 A | 11/1996 | Estes | |
| 5,578,035 A | 11/1996 | Lin | |
| 5,601,558 A | 2/1997 | Torrie et al. | |
| 5,603,714 A * | 2/1997 | Kaneda et al. | 606/272 |
| 5,607,426 A | 3/1997 | Ralph et al. | |
| 5,607,428 A | 3/1997 | Lin | |
| 5,611,688 A | 3/1997 | Hanosh | |
| 5,643,265 A | 7/1997 | Errico et al. | |
| 5,643,321 A | 7/1997 | McDevitt | |
| 5,690,629 A * | 11/1997 | Asher et al. | 606/265 |
| 5,702,391 A | 12/1997 | Lin | |
| 5,728,127 A * | 3/1998 | Asher et al. | 606/292 |
| 5,733,284 A * | 3/1998 | Martin | 606/248 |
| 5,735,853 A | 4/1998 | Olerud | |
| 5,741,258 A | 4/1998 | Klaue et al. | |
| 5,759,184 A | 6/1998 | Santangelo | |
| 5,769,852 A | 6/1998 | Br.ang.nemark | |
| 5,797,912 A | 8/1998 | Runciman et al. | |
| 5,810,823 A * | 9/1998 | Klaue et al. | 606/289 |
| 5,843,082 A | 12/1998 | Yuan et al. | |
| 5,849,004 A | 12/1998 | Bramlet | |
| 5,876,402 A | 3/1999 | Errico et al. | |
| 5,899,905 A * | 5/1999 | Errico et al. | 606/256 |
| 5,902,303 A | 5/1999 | Eckhof et al. | |
| 5,904,683 A | 5/1999 | Pohndorf et al. | |
| 5,925,047 A * | 7/1999 | Errico et al. | 606/65 |
| 5,931,621 A | 8/1999 | Griffith et al. | |
| 5,931,838 A | 8/1999 | Vito | |
| 5,947,969 A * | 9/1999 | Errico et al. | 606/308 |
| 5,954,722 A | 9/1999 | Bono | |
| 5,964,760 A * | 10/1999 | Richelsoph | 606/279 |
| 5,976,139 A | 11/1999 | Bramlet | |
| 6,017,345 A | 1/2000 | Richelsoph | |
| 6,030,389 A | 2/2000 | Wagner et al. | |
| 6,036,693 A | 3/2000 | Yuan et al. | |
| 6,039,740 A | 3/2000 | Olerud et al. | |
| 6,077,264 A | 6/2000 | Chemello et al. | |
| 6,132,464 A * | 10/2000 | Martin | 623/17.15 |
| 6,168,597 B1 | 1/2001 | Biedermann et al. | |
| 6,183,474 B1 | 2/2001 | Bramlet et al. | |
| 6,206,882 B1 | 3/2001 | Cohen | |
| 6,235,033 B1 | 5/2001 | Brace et al. | |
| 6,241,731 B1 | 6/2001 | Fiz | |
| 6,261,291 B1 | 7/2001 | Talaber et al. | |
| 6,273,889 B1 | 8/2001 | Richelsoph | |
| 6,322,562 B1 | 11/2001 | Wolter et al. | |
| 6,331,179 B1 | 12/2001 | Freid et al. | |
| 6,383,187 B2 * | 5/2002 | Tormala et al. | 606/305 |
| 6,402,756 B1 | 6/2002 | Ralph et al. | |
| 6,423,067 B1 | 7/2002 | Eisermann | |
| 6,428,542 B1 | 8/2002 | Michelson | |
| 6,443,954 B1 | 9/2002 | Bramlet et al. | |
| 6,447,513 B1 | 9/2002 | Griggs | |
| 6,447,546 B1 | 9/2002 | Bramlet et al. | |
| 6,454,769 B2 | 9/2002 | Wagner et al. | |
| 6,488,683 B2 * | 12/2002 | Lieberman | 606/263 |
| 6,551,320 B2 * | 4/2003 | Lieberman | 606/263 |
| 6,575,975 B2 | 6/2003 | Brace et al. | |
| 6,595,993 B2 | 7/2003 | Donno et al. | |
| 6,599,290 B2 | 7/2003 | Bailey et al. | |
| 6,602,255 B1 | 8/2003 | Campbell et al. | |
| 6,623,484 B2 * | 9/2003 | Betz et al. | 606/279 |
| 6,648,889 B2 | 11/2003 | Bramlet et al. | |
| 6,660,008 B1 | 12/2003 | Foerster et al. | |
| 6,668,688 B2 | 12/2003 | Zhao et al. | |
| 6,679,883 B2 | 1/2004 | Hawkes et al. | |
| 6,695,846 B2 | 2/2004 | Richelsoph et al. | |
| 6,712,852 B1 * | 3/2004 | Chung et al. | 623/17.11 |
| 6,719,795 B1 * | 4/2004 | Cornwall et al. | 623/17.11 |
| 6,730,093 B2 * | 5/2004 | Saint Martin | 606/303 |
| 6,890,334 B2 | 5/2005 | Brace et al. | |
| 6,932,834 B2 | 8/2005 | Lizardi et al. | |
| 6,945,975 B2 | 9/2005 | Dalton | |
| 6,964,664 B2 | 11/2005 | Freid et al. | |
| 6,979,334 B2 | 12/2005 | Dalton | |
| 6,989,013 B2 | 1/2006 | Pisharodi | |
| 7,001,389 B1 | 2/2006 | Navarro et al. | |
| 7,052,499 B2 | 5/2006 | Steger et al. | |
| 7,074,239 B1 * | 7/2006 | Cornwall et al. | 623/17.11 |
| 7,118,572 B2 | 10/2006 | Bramlet et al. | |
| 7,381,213 B2 | 6/2008 | Lizardi | |
| 7,481,828 B2 * | 1/2009 | Mazda et al. | 606/263 |
| 7,615,069 B2 * | 11/2009 | Paul | 606/287 |
| 7,722,650 B2 * | 5/2010 | Ashman | 606/265 |
| 7,879,036 B2 | 2/2011 | Biedermann et al. | |
| 7,892,260 B2 * | 2/2011 | Mahoney et al. | 606/265 |
| 7,905,908 B2 | 3/2011 | Cragg et al. | |
| 7,967,848 B2 * | 6/2011 | Abdelgany | 606/266 |
| 8,048,116 B2 * | 11/2011 | Lee | 606/247 |
| 8,211,156 B2 * | 7/2012 | Andersen et al. | 606/309 |
| 8,221,479 B2 * | 7/2012 | Glazer et al. | 606/326 |
| 8,277,485 B2 * | 10/2012 | Krishna et al. | 606/246 |
| 8,282,675 B2 * | 10/2012 | Maguire et al. | 606/289 |
| 8,343,200 B2 * | 1/2013 | Khanna et al. | 606/304 |
| 8,361,130 B2 | 1/2013 | Daly et al. | |
| 8,475,502 B2 * | 7/2013 | Paul | 606/272 |
| 8,486,121 B2 * | 7/2013 | Biedermann et al. | 606/313 |
| 8,506,608 B2 * | 8/2013 | Cerynik et al. | 606/300 |
| 8,623,062 B2 * | 1/2014 | Kondrashov | 606/280 |
| 8,690,924 B2 * | 4/2014 | Chin et al. | 606/264 |
| 8,734,497 B2 * | 5/2014 | Goel et al. | 606/310 |
| 2001/0021851 A1 | 9/2001 | Eberlein et al. | |
| 2002/0058939 A1 | 5/2002 | Wagner et al. | |
| 2003/0078583 A1 | 4/2003 | Biedermann et al. | |
| 2003/0083657 A1 * | 5/2003 | Drewry et al. | 606/61 |
| 2003/0187440 A1 | 10/2003 | Richelsoph et al. | |
| 2003/0199876 A1 | 10/2003 | Brace et al. | |
| 2003/0208204 A1 | 11/2003 | Bailey et al. | |
| 2003/0225409 A1 | 12/2003 | Freid et al. | |
| 2004/0019353 A1 | 1/2004 | Freid et al. | |
| 2004/0087951 A1 | 5/2004 | Khalili | |
| 2004/0097935 A1 | 5/2004 | Richelsoph et al. | |

(56) References Cited

U.S. PATENT DOCUMENTS

| | | |
|---|---|---|
| 2004/0106925 A1 | 6/2004 | Culbert |
| 2004/0111088 A1* | 6/2004 | Picetti et al. ............... 606/61 |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0127904 A1 | 7/2004 | Konieczynski et al. |
| 2004/0172022 A1 | 9/2004 | Landry et al. |
| 2004/0181227 A1 | 9/2004 | Khalili |
| 2004/0193157 A1 | 9/2004 | Falahee |
| 2004/0193162 A1 | 9/2004 | Bramlet et al. |
| 2004/0254579 A1 | 12/2004 | Buhren et al. |
| 2005/0004574 A1 | 1/2005 | Muckter |
| 2005/0010218 A1 | 1/2005 | Dalton |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0049593 A1 | 3/2005 | Duong et al. |
| 2005/0059971 A1 | 3/2005 | Michelson |
| 2005/0065526 A1* | 3/2005 | Drew et al. ............... 606/72 |
| 2005/0143737 A1 | 6/2005 | Pafford et al. |
| 2005/0149027 A1 | 7/2005 | Campbell et al. |
| 2005/0154392 A1 | 7/2005 | Medoff et al. |
| 2005/0192577 A1 | 9/2005 | Mosca et al. |
| 2005/0228386 A1 | 10/2005 | Ziolo et al. |
| 2005/0228387 A1* | 10/2005 | Paul ............... 606/72 |
| 2005/0267474 A1 | 12/2005 | Dalton |
| 2005/0273105 A1 | 12/2005 | Konieczynski et al. |
| 2005/0277937 A1 | 12/2005 | Leung et al. |
| 2005/0283152 A1 | 12/2005 | Lindemann et al. |
| 2006/0009770 A1 | 1/2006 | Speirs et al. |
| 2006/0015104 A1 | 1/2006 | Dalton |
| 2006/0025768 A1 | 2/2006 | Iott et al. |
| 2006/0100626 A1 | 5/2006 | Rathbun et al. |
| 2006/0106390 A1* | 5/2006 | Jensen et al. ............... 606/73 |
| 2006/0116678 A1 | 6/2006 | Impellizzeri |
| 2006/0122602 A1 | 6/2006 | Konieczynski et al. |
| 2006/0122604 A1 | 6/2006 | Gorhan et al. |
| 2006/0149249 A1 | 7/2006 | Mathoulin et al. |
| 2006/0149256 A1 | 7/2006 | Wagner et al. |
| 2006/0149258 A1 | 7/2006 | Sousa |
| 2006/0161157 A1 | 7/2006 | Mosca et al. |
| 2006/0217717 A1* | 9/2006 | Whipple ............... 606/61 |
| 2007/0038210 A1 | 2/2007 | Yaldo |
| 2007/0038219 A1 | 2/2007 | Matthis et al. |
| 2007/0073295 A1 | 3/2007 | Biedermann et al. |
| 2007/0162023 A1* | 7/2007 | Schock ............... 606/72 |
| 2007/0198018 A1 | 8/2007 | Biedermann et al. |
| 2007/0270816 A1* | 11/2007 | Rezach ............... 606/61 |
| 2007/0270817 A1* | 11/2007 | Rezach ............... 606/61 |
| 2008/0086130 A1 | 4/2008 | Lake et al. |
| 2008/0086131 A1 | 4/2008 | Daly et al. |
| 2008/0183220 A1 | 7/2008 | Glazer et al. |
| 2008/0255618 A1 | 10/2008 | Fisher et al. |
| 2008/0255622 A1* | 10/2008 | Mickiewicz et al. ......... 606/319 |
| 2008/0300630 A1* | 12/2008 | Bonnema et al. ............. 606/246 |
| 2009/0099601 A1 | 4/2009 | Aferzon et al. |
| 2009/0192551 A1* | 7/2009 | Cianfrani et al. ............. 606/301 |
| 2009/0192553 A1 | 7/2009 | Maguire et al. |
| 2009/0318973 A1* | 12/2009 | Moulin et al. ................ 606/278 |
| 2010/0069969 A1* | 3/2010 | Ampuero et al. ............. 606/301 |
| 2010/0082067 A1* | 4/2010 | Kondrashov .................. 606/264 |
| 2010/0106195 A1* | 4/2010 | Serhan et al. ................ 606/279 |
| 2010/0228301 A1* | 9/2010 | Greenhalgh et al. .......... 606/313 |
| 2010/0292734 A1* | 11/2010 | Bullard ........................ 606/246 |
| 2011/0152937 A1* | 6/2011 | Trieu ............................ 606/264 |
| 2011/0178552 A1* | 7/2011 | Biscup et al. ................ 606/246 |
| 2013/0030474 A1* | 1/2013 | Chaput ........................ 606/305 |
| 2014/0066991 A1* | 3/2014 | Marik et al. .................. 606/279 |

OTHER PUBLICATIONS

Suk, et al., "Unilateral Versus Bilaterial Pedicle Screw Fixation in Lumbar Spinal Fusion", SPINE, vol. 25, No. 14, pp. 1843-1847, 2000.

Chen, et al., "Biomechanical Analysis of Unilateral Fixation With Interbody Cages", SPINE, vol. 30, No. 4, pp. E92-E96, 2005.

Foley, et al., "Percutaneous pedicle screw fixation of the lumbar spine", Neurosurg Focus 10 (4), Article 10, pp. 108, 2001.

Grubb, et al., "Biomechanical Evaluation of Anterior Cervical Spine Stabilization," SPINE 1998, vol. 23, No. 8, pp. 886-892.

Harris, et al., "Transforaminal Lumbar Interbody Fusion", SPINE, vol. 29, No. 4, pp. E65-E70, 2004.

Keller, et al., "The ComPact UniLock 2.0/2.4 system and its clinical application in small animal orthopedics", Vet Comp Orthop Traumatol, pp. 83-93, Feb. 2005.

Law, et al., "Caudo-Cephalad Loading of Pedicle Screws: Mechanisms of Loosening and Methods of Augmentation," SPINE 1993, vol. 18, No. 16, pp. 2438-2443.

Lehmann, et al., "Biomechanical comparison of anterior cervical spine locked and unlocked plate-fixation systems", Eur Spine J. 2005, vol. 14, pp. 243-249.

Spivak, et al., "The Effect of Locking Fixation Screws on the Stability of Anterior Cervical Plating", SPINE 1999, vol. 24, No. 4, pp. 334-338.

Yang, et al., "Biomechanical comparision of the stable efficacy of two anterior plating systems", Clinical Biomechanics, vol. 18(6), pp. 59-66, Jul. 2003.

* cited by examiner

BONE SCREW FIXATION

CROSS-REFERENCE TO RELATED APPLICATIONS

This application is a divisional of U.S. patent application Ser. No. 11/867,771 filed on Oct. 5, 2007 and entitled "Improved Bone Screw Fixation," which claims priority to U.S. Provisional Application No. 60/828,428 filed on Oct. 6, 2006 and entitled "Improved Bone Screw Fixation," each of which is hereby incorporated by reference in its entirety.

BACKGROUND

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Other causes of an abnormally shaped spine include trauma and spinal degeneration with advancing age. Early techniques for correcting such deformities utilized external devices that applied force to the spine in an attempt to reposition the vertebrae. These devices, however, resulted in severe restriction and in some cases immobility of the patient. Furthermore, current external braces have limited ability to correct the deformed spine and typically only prevent progression of the deformity. Thus, to avoid this need, doctors developed several internal fixation techniques to span across multiple vertebrae and force the spine into a desired orientation. Additional fixation is beneficial in cases in which the bone quality is poor, such as patients with osteoporotic bone. The poor bone quality reduces the strength of the bone to implant interface.

To fix the spine, surgeons attach one or more fixation elements (typically rods or plates) to the spine at several fixation sites to correct and stabilize the spinal deformity, prevent reoccurrence of the spinal deformity, and stabilize weakness in trunks that results from degenerative discs and joint disease, deficient posterior elements, spinal fracture, and other debilitating problems. Bone screws are typically used to anchor the spinal rods or plates at the various fixation sites. Once anchored, the rod-based systems are under stress and subjected to significant forces, known as cantilever pull-out forces. As a result, surgeons are always concerned about the possibility of the implant loosening or the bone screws pulling out of the bone. Thus, surgeons generally seek to attach implants in the most secure and stable fashion possible while at the same time addressing a patient's specific anatomy. In some instances, motion of the spine causes stress at the interface between the bone screws and the bone, resulting in loosening of the bone screws.

Accordingly, there is a need in this art for improved methods and devices for bone screw fixation.

SUMMARY

The present invention generally provides methods and device for fixing a bone screw to bone. In one embodiment, a bone fixation device is provided and includes a receiving head having a recess adapted to seat a spinal rod therein and a shank extending distally from the receiving head. An anti-rotation mechanism can be located distal of a distal end of the receiving head and around a proximal portion of the shank, and it can be configured to interact with bone to prevent rotation of at least a portion of the bone screw relative to the bone.

The anti-rotation mechanism can have a variety of configurations. In one exemplary embodiment, the anti-rotation mechanism can be in the form of one or more spikes extending distally from the distal end of the receiving head and adapted to engage bone. In another embodiment, the receiving head can have a substantially rectangular shape such that the rectangular shape forms an anti-rotation mechanism that is adapted to engage bone. In another exemplary embodiment, the anti-rotation mechanism can be in the form of a washer adapted to deform between the head and bone when the bone screw is inserted into bone. The washer can include fixation features to engage bone. In yet another exemplary embodiment, the anti-rotation mechanism can be in the form of a generally hemi-spherical member disposed around the shank. The hemi-spherical member can have surface features for engaging bone and/or a coating disposed thereon for promoting bone ingrowth into the hemi-spherical member. In another exemplary embodiment, the anti-rotation mechanism can be in the form of one or more extensions coupled to the proximal portion of the shank and adapted to protrude from the shank when a deployment member is disposed within a lumen formed in the shank. In another exemplary embodiment, the anti-rotation mechanism can be in the form of a threaded member that is disposed around the shank and that includes threads that extend in a direction opposite to a direction of the threads disposed around the shank.

Methods for bone screw fixation are also provided and in one embodiment the method can include inserting a bone screw into bone to cause an anti-rotation mechanism located distal of a distal end of a receiving head of the bone screw and around a proximal portion of a shank of the bone screw to engage bone surrounding the bone screw. The method can further include positioning a spinal connector within the receiving head, and applying a locking mechanism to lock the rod within the receiving head. In one embodiment, the anti-rotation mechanism can be in the form of at least one spike movably coupled to the head, and applying the locking mechanism can cause the at least one spike to extend from the receiving head and into bone. In another embodiment, the anti-rotation mechanism can be in the form of at least one spike movably disposed within the shank of the bone screw, and advancing a deployment mechanism through the shank of the bone screw can cause the at least one spike to extend from the bone screw and into bone. In yet another embodiment, the anti-rotation mechanism can be in the form of a deformable washer that is disposed around the shank, and inserting the bone screw into bone can cause the deformable washer to deform between the receiving head and the bone. In other aspects, the anti-rotation mechanism can be in the form of a hemi-spherical member that is disposed around the shank and that is effective to engage bone disposed around the shank. The hemi-spherical member can include a plurality of surface features formed thereon that extend into and engage bone disposed around the shank, and/or it can include a coating formed thereon that promotes bone ingrowth into the hemi-spherical member. In yet another embodiment, the anti-rotation mechanism can be in the form of a threaded member, and inserting the bone screw into bone can include rotating the threaded member in a first direction to insert the threaded member into bone, and inserting the shank of the bone screw through a lumen formed in the threaded member and rotating the shank of the bone screw in a second direction opposite to the first direction to insert the shank of the bone screw into bone.

In another embodiment, a method of fixing a bone screw to bone is provided and includes implanting a bone anchor into a vertebra. The bone anchor can have a receiving head configured for receiving a spinal rod and a shank extending from the receiving head. The receiving head can have a substantially rectangular shape such that opposed sidewalls of the receiving head engage a spinous and transverse process of a vertebra to prevent rotation of the receiving head relative to the vertebra.

BRIEF DESCRIPTION OF THE DRAWINGS

The invention will be more fully understood from the following detailed description taken in conjunction with the accompanying drawings, in which.

DETAILED DESCRIPTION

Figure 1A:
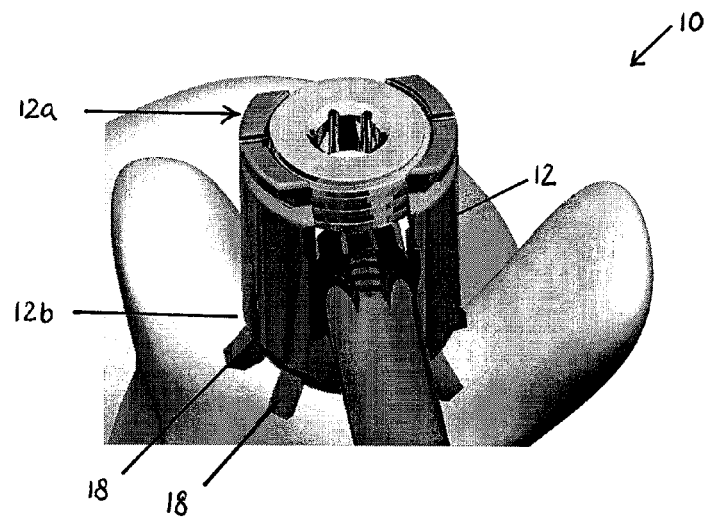
FIG. 1A is perspective view of one exemplary embodiment of a bone screw implanted in bone an having an anti-rotation mechanism that is in the form of several spikes extending distally from a distal end of a receiving head of the bone screw.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for spinal fixation. In one exemplary embodiment, the methods and devices provide an anti-rotation mechanism located on a bone anchor for preventing rotation of at least a portion of the bone anchor relative to bone. The methods and devices are particularly useful for unilateral fixation, in which one or more levels of the spine are stabilized along a single lateral side of the spine. An anti-rotation mechanism is particularly desirable with unilateral fixation, as the natural forces through the spine are centered down the middle of the spine and thus the anti-rotation mechanism helps to stabilize the bone anchor and provide a more secure fixation.

A person skilled in the art will appreciate that, while the methods and devices are particularly useful for unilateral fixation, the methods and devices can be used in various procedures in which it is desirable to provide a more secure connection between a bone anchor and bone. A person skilled in the art will also appreciate that the term unilateral or bilateral fixation is intended to include both rigid fixation in which movement between adjacent vertebrae is prevented, and dynamic fixation in which adjacent vertebrae are stabilized relative to one another but a limited amount of motion is allowed between the adjacent vertebrae. With rigid fixation, for example, one or more bone anchors can be coupled to one another by a rigid spinal connector, such as a spinal rod. With dynamic fixation, for example, one or more bone anchors can be coupled to one another by a dynamic spinal connector, such as a flexible spinal rod, a dynamic or flexible spinal plate, or other devices that will allow motion between the adjacent vertebrae. Commonly-owned U.S. patent application Ser. No. 11/539,302 filed on Oct. 6, 2006 and entitled "Torsionally Stable Fixation," by Lake et al., which is hereby incorporated by reference in its entirety, discloses various exemplary spinal connectors that can be used with the spinal anchors disclosed herein. The spinal connectors are particularly configured for use during fixation, and thus can further provide a more secure spinal fixation construct.

FIGS. 1A-10E illustrate various exemplary embodiments of a bone anchor having an anti-rotation mechanism. While the illustrated bone anchors are in the form of bone screw, a person skilled in the art will appreciate that the various anti-rotation mechanism disclosed herein can be used on a variety of bone anchors, including hooks, plates, etc. In general, the bone screws illustrated in FIGS. 1A-10E each include a receiving head having a recess that is adapted to seat a spinal connector therein, and a shank extending distally from the receiving head. The recess is formed in a proximal end of the head, and a distal end of the head is coupled to a proximal end of the shank. The shank can be fixedly mated to the head, or it can be movably coupled to the head to allow polyaxial movement of the shank. The distal portion of the shank extending from the head is configured to be inserted in bone, and thus it can include, for example, threads extending therearound for engaging bone. The bone screw can also include a locking mechanism, such as a set screw, for locking a rod within the recess of the head. The head can include threads formed therein or therearound for mating with the set screw. The locking mechanism can, however, have a variety of other configurations and various locking techniques known in the art can be used to mate the locking mechanism to the head and thereby lock a spinal connector therein. FIGS. 1A-10E also illustrate various anti-rotation mechanisms for preventing rotation of at least a portion of a bone screw relative to bone.

Figure 1B:
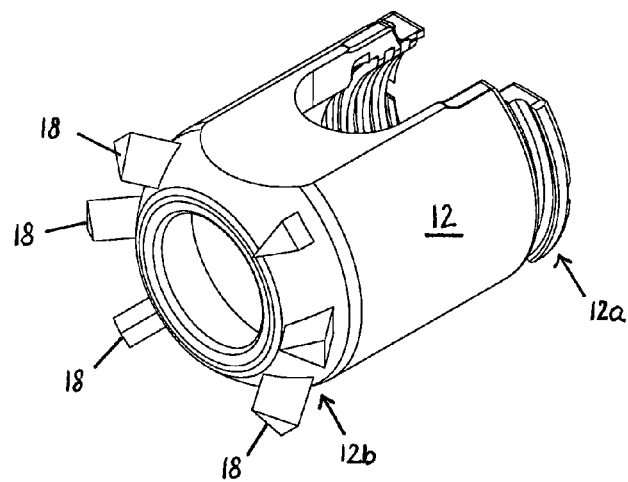
FIG. 1B is a perspective view of the head of the bone screw shown in FIG. 1A.

FIGS. 1A-1B illustrate one exemplary embodiment of a bone screw 10 having an anti-rotation mechanism. In general, the bone screw 10 includes a receiving head 12 and a shank (not shown) as described above. In this embodiment, the anti-rotation mechanism is in the form of several teeth or spikes 18 that are integrally formed on and that extend distally from a distal end 12b of the receiving head 12. The spikes 18 can have a variety of shapes and sizes, but in the illustrated embodiment each spike 18 is in the form of an elongate triangular member that extends radially outward from the distal end 12b of the receiving head 12. The spikes 18 can be also positioned at various locations on the head 12. As shown in FIG. 1, the spikes 18 are spaced a distance apart from one another around a perimeter of a distal end 12b of the receiving head 12. In use, the spikes 18 are configured to engage bone and thereby prevent rotation of the head 12. In particular, since the shank (not shown) can rotate independent of the head 12, the head 12 can be remain in a fixed position relative to bone while the shank is rotatably driven into the bone to thereby drive the spikes 18 on the head 12 into engagement with the bone. The spikes 18 will thus prevent rotation of the head 12 relative to bone. As shown, the spikes 18 may be angled to provide improved holding strength.

Figure 2A:
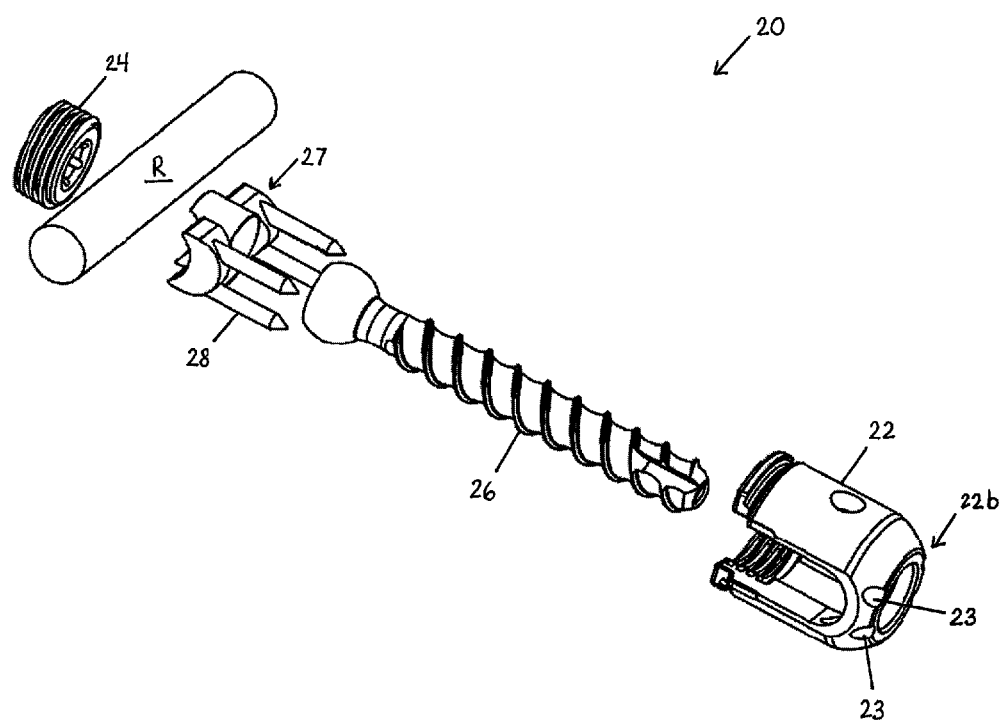
FIG. 2A is an exploded perspective view of another embodiment of a bone screw having an anti-rotation mechanism in the form of spikes that are adapted to extend from a receiving head of the bone screw to engage bone.
Figure 2B:
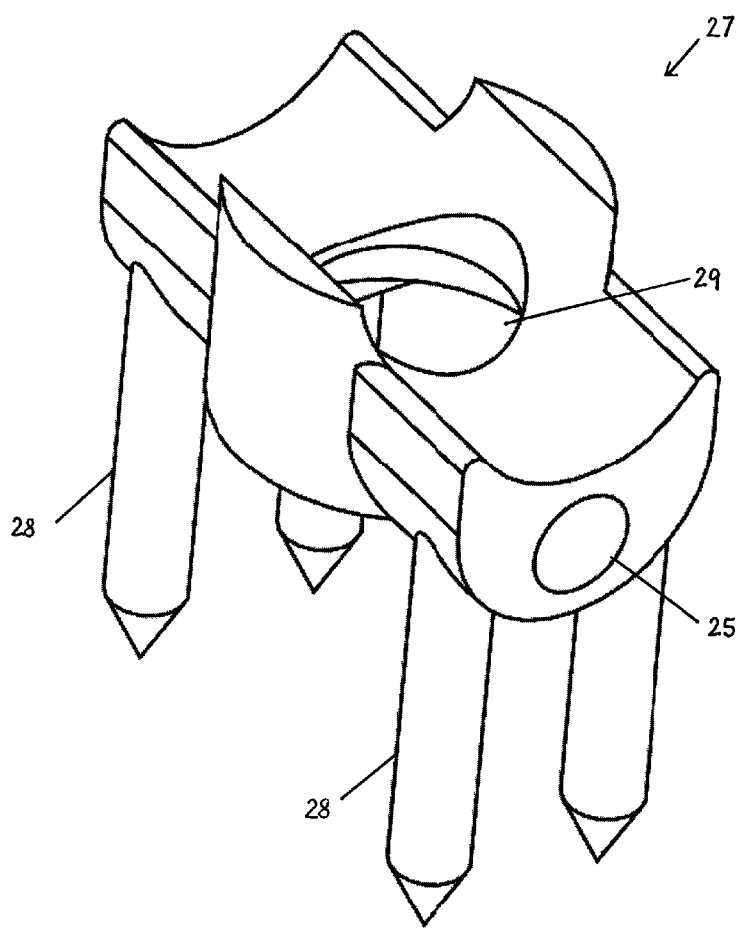
FIG. 2B is a perspective view of a retaining member of the bone screw of FIG. 2A.
Figure 2C:
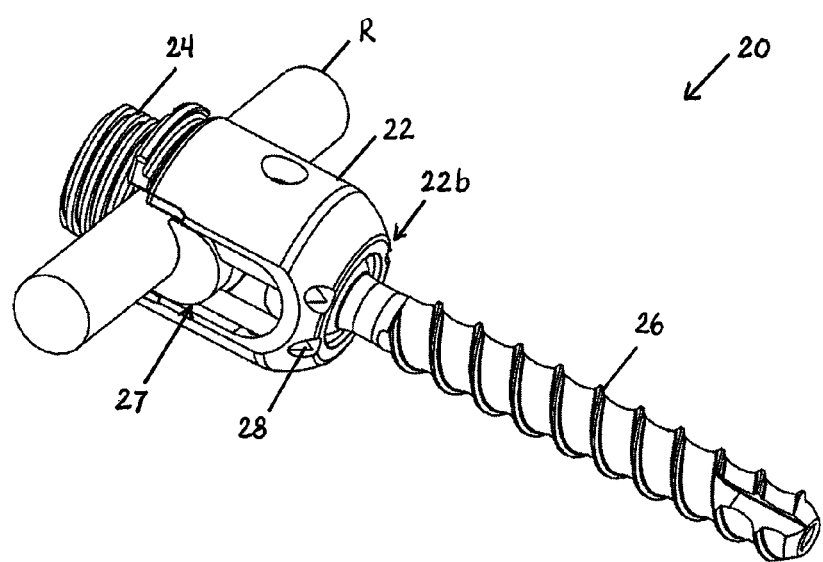
FIG. 2C is a perspective view of the bone screw of FIG. 2A, showing the spikes in a first retracted position in which the spikes are located within the receiving head of the bone screw.
Figure 2D:
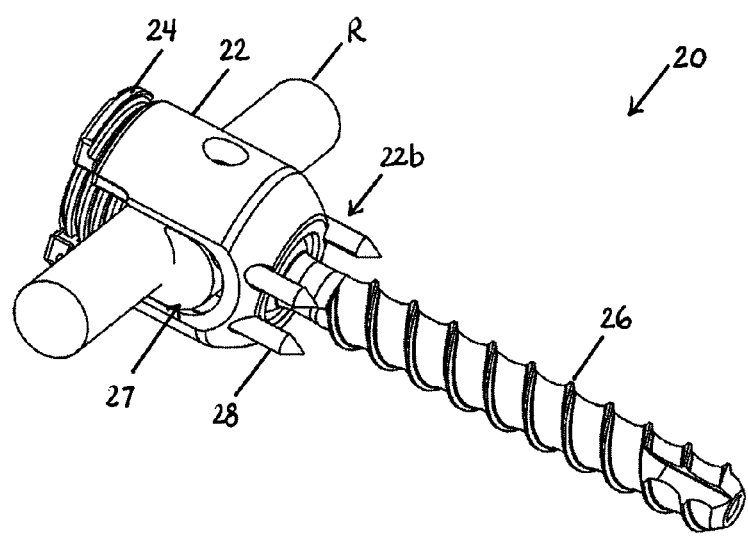
FIG. 2D is a perspective view of the bone screw of FIG. 2A, showing the spikes in the second extended position in which the spikes extend from the receiving head to engage bone.

In another embodiment, as shown in FIGS. 2A-2D, the bone screw 20 can include one or more teeth or spikes 28 that are movably disposed within the head 22 of the bone screw 20. In particular, the spikes 28 can be configured to move between a first retracted position, as shown in FIG. 2C, in which the spikes 28 are fully disposed within the head 22, and a second extended position, as shown in FIG. 2D, in which the spikes 28 extend distally from the head 22. In order to allow such movement of the spikes 28, the distal end 22b of the head 22 can include several openings or bores 23 formed therein for movably receiving the spikes 28. The spikes 28 can include a proximal end 28a having a flange or enlarged region that is larger than the size of the bores or openings to retain the spikes 28 within the head 22. Alternatively, a proximal end of each spike 28 can be coupled to one another by a ring-shaped member that is seated within a distal portion of the head 22. In an exemplary embodiment, as shown in more detail in FIG. 2B, the retaining member 27 is sized and shaped to be housed within the head 22 of the bone screw 20, and it can have a convex proximal surface adapted to seat the spinal rod therein. The spikes 28 can be coupled to the retaining member 27 in such a configuration as to correspond to the bores 23 formed in the head 22 to allow the bores 23 to receive the spikes 28 when the spikes 28 are moved into the second extended position. The spikes 28 can be unitary with the retaining member 27 or they can be separate components, and the spikes 28 can be fixedly or removably coupled to the retaining member 27. The retaining member 27 can also optionally include a central bore 29 formed therethrough to allow a driver to be inserted through the retaining member 27 to drive the bone screw 20 into bone.

In use, the retaining member 27 with spikes 28 can be freely disposed within the head 22 such that the retaining member 27 and spikes 28 will move to the retracted position when the screw is being driven into bone. However, in an exemplary embodiment, the retaining member 27 is held in a retracted position during deployment of the screw. For example, the retaining member 27 can include a retaining feature adapted to hold the retaining member 27 and the spikes 28 within the head 22. In the illustrated embodiment, the retaining member 27 can include one or more bores (not shown) formed on the curved walls of the retaining member 27. The head 22 can include one or more corresponding protrusions that are adapted to extend into and engage the bores. The protrusions can be positioned in a location that keeps the retaining member 27 and the spikes 28 fully disposed within the head. For example, the protrusions can be located so that the distal end of the spikes 28 does not extend through the bores 23 formed in the head 22. In an exemplary embodiment, the protrusions are positioned just distal of the threads formed within the head 22. A person skilled in the art will appreciate that protrusions and/or bores can be located at any position within the head 22 and/or on the retaining member 27 to allow the retaining member 27 and the spikes 28 to be held in the retracted position. In use, in order to move the retaining member 27 and the spikes 28 into the second extended position, a rod R which gets seated in the head 22 can push the retaining member out of engagement with the protrusions, thus allowing the retaining member 27 and the spikes 28 to move distally towards the second extended position in which the spikes 28 will engage bone.

In other embodiments, the retaining member can be inserted into the head 22 of the bone screw 20 after the bone screw 20 is driven into bone. For example, the retaining member 27 can include one or more features, such as bores 29, formed therein that are adapted to removably couple to the inserter tool, thus allowing the inserter tool to grasp and deliver the retaining member to the head 22. The inserter tool can also or alternatively be used to hold the retaining member in the retracted position while the screw 20 is driven into bone. A person skilled in the art will appreciate that any technique can be used to retain the retaining member 27 and the spikes 28 in the head 22 of the bone screw during insertion of the bone screw into bone, or alternatively the retaining member 27 can float within the head 22. In such an embodiment, the retaining member 27 and spikes 28 can simply move to the retracted position as the screw 20 is driven into bone.

FIGS. 2C and 2D illustrated the spikes 28 in use. As shown in FIG. 2C, the spikes 28 are in the retracted position. The spikes 28 can be moved into the second extended position using the spinal rod R, as described above. In an exemplary embodiment, the spinal rod R is reduced into the head of the bone screw using a locking element, such as a set screw 24. As the set screw 24 is mated to the receiving head 22, the set screw 24 will move the spinal rod R distally within the recess in the head 22. As a result, the spinal rod R will force the spikes 28 to move from the first retracted position, shown in FIG. 2C, to the second extended position, shown in FIG. 2D, in which the spikes 28 extend through the bores 23 and protrude distally from the head 22, thereby causing the spikes 28 to engage bone and thus prevent rotation of the head 22 of the bone screw 20 relative to the bone. The spinal rod R being seated in the head 22 of the bone screw 20 will keep the spikes 28 in the second extended position to maintain their engagement with bone.

While not shown, in other embodiments the spinal anchor can optionally include a compression element disposed within the head 22 of the bone screw 20. As the set screw 24 locks the rod R within the head 22, the rod R will abut against and push the compression element distally within the head 22 to force the spikes 28 to extend through the bores and protrude distally from the head 22. In another embodiment, at least a portion of the spikes 28 can be semi-flexible or flexible to allow the spikes 28 to deform as the spikes 28 are extended from the head 22 to provide additional holding strength. A person skilled in the art will appreciate any technique can be used to move and lock the spikes 28 into the second extended position. For example, a secondary instrument could deploy the spikes 28 or retract the spikes 28 for implant removal, preferably with the rod R in it's final placement.

Figure 2E:
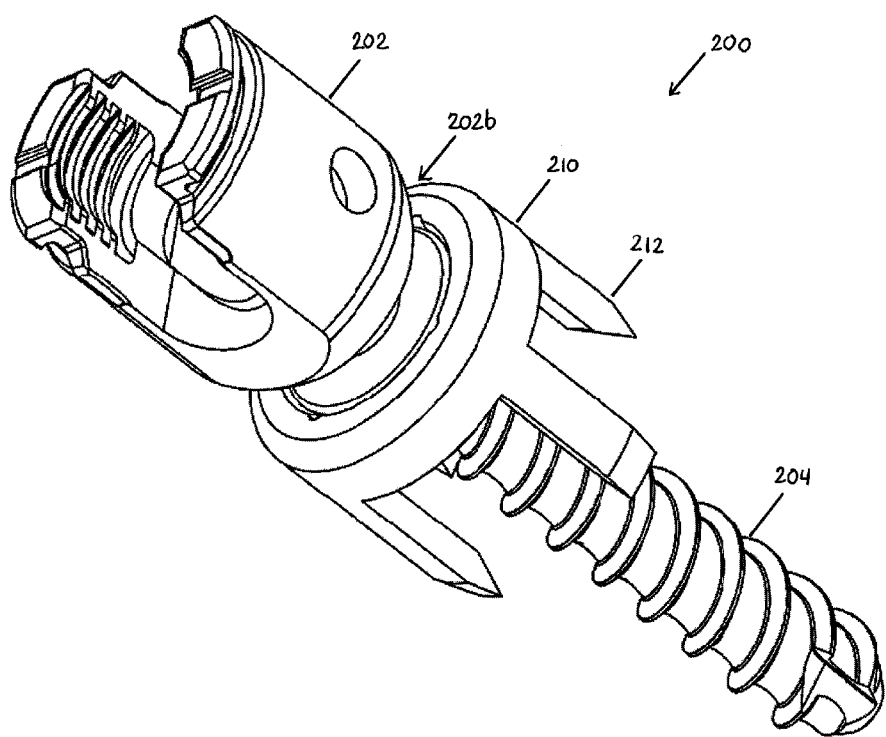
FIG. 2E is a perspective view of another embodiment of a bone screw having an anti-rotation mechanism in the form of a staple disposed around a shank of the bone screw.
Figure 2F:
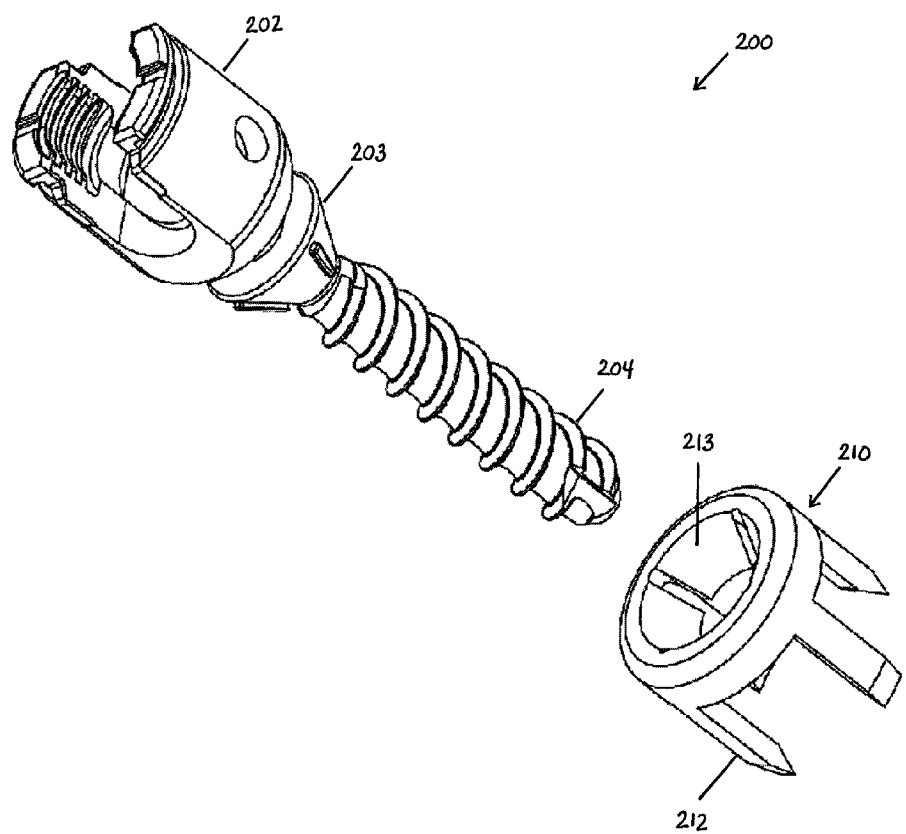
FIG. 2F is a partially exploded perspective view of the bone screw of FIG. 2E.

In another embodiment, rather than having spikes formed on or disposed within the receiving head, a separate member can be removably disposed around the shank and it can be configured to mate with the receiver head. By way of non-limiting example, FIGS. 2E and 2F illustrate another embodiment of a bone screw 200 having a staple 210 that is disposed around the shank 204 of the bone screw 200 at a location just proximal to the distal end 202b of the head 202. The staple 210 has a generally hollow circular body with several distally-extending spikes 212 formed thereon and configured to extend into and engage bone. In order to prevent rotation between the staple 210 and the bone screw 200, the head 202 of the bone screw 200 can include a mating feature formed thereon for mating with a corresponding mating feature formed on the staple 210. While various mating techniques can be used, including techniques disclosed herein with respect to other embodiments, in the illustrated embodiment the head 202 includes a tapered portion 203 having several ridges formed thereon, and an inner lumen 213 extending through the staple 210 has a complementary tapered shape with several grooves formed therein for receiving the ridges. In use, the shank 204 can rotated independent of the staple 210 and the head 202, thus allowing the shank 204 to be threaded into bone while driving the staple 210 into bone, and driving the head 202 into engagement with the staple 210.

Figure 3A:
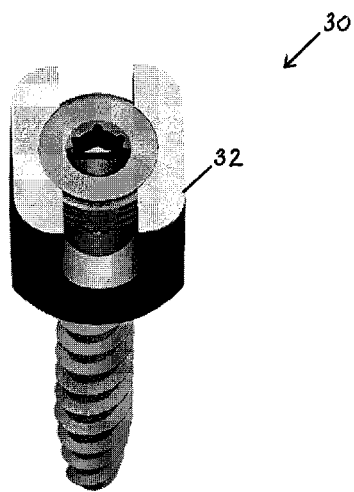
FIG. 3A is a top perspective view of another exemplary embodiment of a bone screw having a substantially rectangular-shaped receiving head that functions as an anti-rotation mechanism.
Figure 3B:
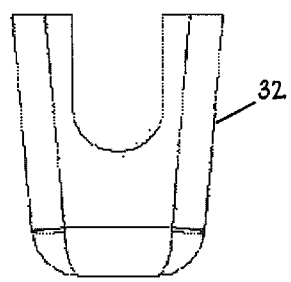
FIG. 3B is a side view of the receiving head of the bone screw of FIG. 3A.
Figure 4:
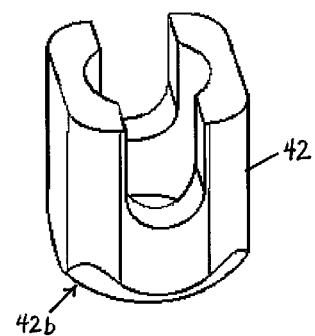
FIG. 4 is a perspective view of another embodiment of a receiving head that can function as an anti-rotation mechanism.

In another exemplary embodiment, the shape of the head of the bone screw can be modified to form an anti-rotation mechanism. In particular, the head of the bone screw or other anchor can be modified to have a non-cylindrical or asymmetrical shape. FIGS. 3A and 3B illustrate one embodiment of a bone screw 30 having a head 32 with a substantially square or rectangular shape. This allows the head 32 to sit within a recessed or milled region of the bone to thereby engage the bone to prevent rotation of the head 32 relative to the bone, as will be discussed in more detail below. As further shown in FIG. 3B, the head 32 can also optionally be tapered to facilitate insertion of the head 32 into the recessed or milled region of bone. In another embodiment, shown in FIG. 4, the distal end 42b of the head 42 can be rounded or curved to match the contour or anatomy of a bone recess or cavity. A person skilled in the art will appreciate that the head can have any geometry that is adapted to prevent rotation of the head relative to the bone.

Figure 5A:
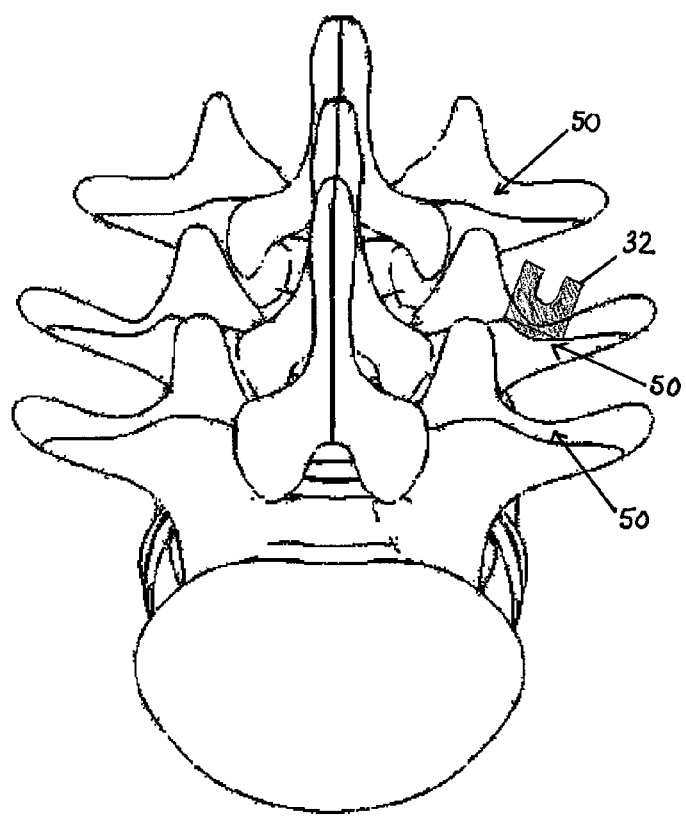
FIG. 5A is a perspective view of a portion of a spine, showing the bone screw of FIGS. 3A and 3B implanted therein.
Figure 5B:
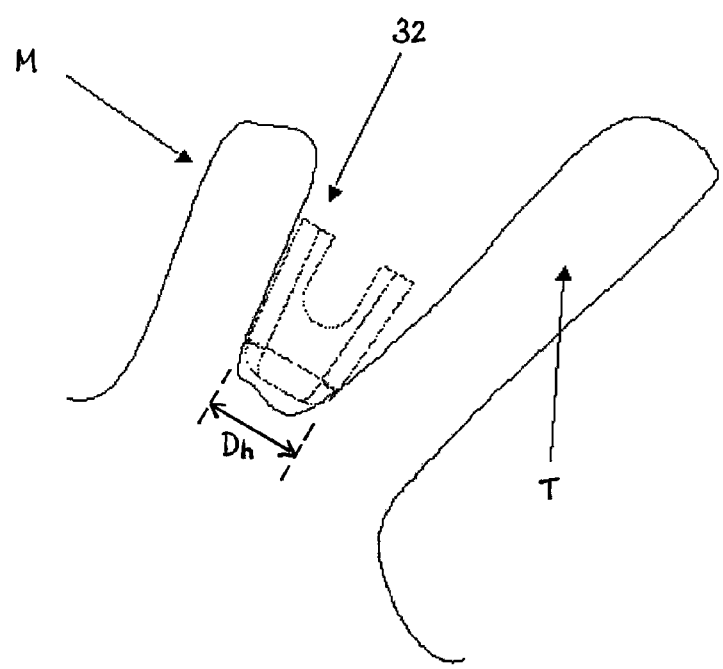
FIG. 5B is a side view of a portion of the spine of FIG. 5A, showing the bone screw of FIGS. 3A and 3B implanted therein.

In use, the asymmetrical head, e.g., head 32 or 42, can be disposed within a recessed region of bone to engage the bone such that the head cannot rotate, or alternatively a recess or cavity can be formed in the bone to receive the head. FIGS. 5A and 5B illustrate one exemplary region of bone located in a spinal column in which a square or other asymmetrical head can be implanted. As shown, the bony anatomy at the saddle point 50 formed by the transverse and mamillary processes can be used to prevent rotation of the head. By way of non-limiting example, head 32 is illustrated disposed within one of the saddle points 50. FIG. 5B illustrates head 32 and saddle point 50 in more detail, showing the mamillary process M and the transverse process T. The use of a tapered 32 head is particularly advantageous in this region of the spine, as the tapered configuration will facilitate mating with the native anatomy. While the angle of the taper can vary, in certain exemplary embodiments the taper has an angle in the range of about 25° to 80°. The base diameter $D_h$ of the head 32, i.e., the diameter at the distal end, can also vary depending on the intended use, but in an exemplary embodiment the base diameter $D_h$ of the head 32 is in the range of about 7 mm to 12 mm.

Figure 6:
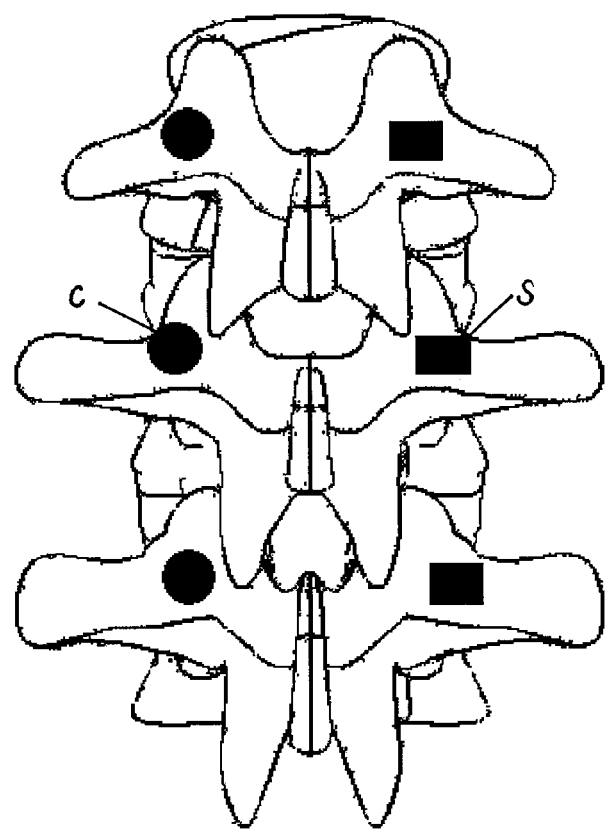
FIG. 6 is a perspective view of a portion of a spine showing various exemplary locations for implanting a bone screw, and/or for forming a cavity for seating a receiving head of a bone screw.

As indicated above, in another embodiment the bone can be milled or otherwise prepared to have a recess or cavity that is configured to seat a head of a bone screw or other bone anchor. FIG. 6 illustrates various exemplary locations along a spine for preparing a recess for receiving and engaging a bone screw. As shown, the bony anatomy in the pedicle region of each vertebrae can be milled to receive a head of a bone screw. The shape of the milled cavity can vary depending on the shape of the head. For example, square or rectangular cavities S can be formed for receiving square or rectangular heads. Alternatively, cylindrical cavities C can be formed for receiving generally cylindrical heads. The various other anti-rotation mechanisms disclosed herein can be used with such cylindrical cavities to prevent rotation of the screw head.

Figure 7:
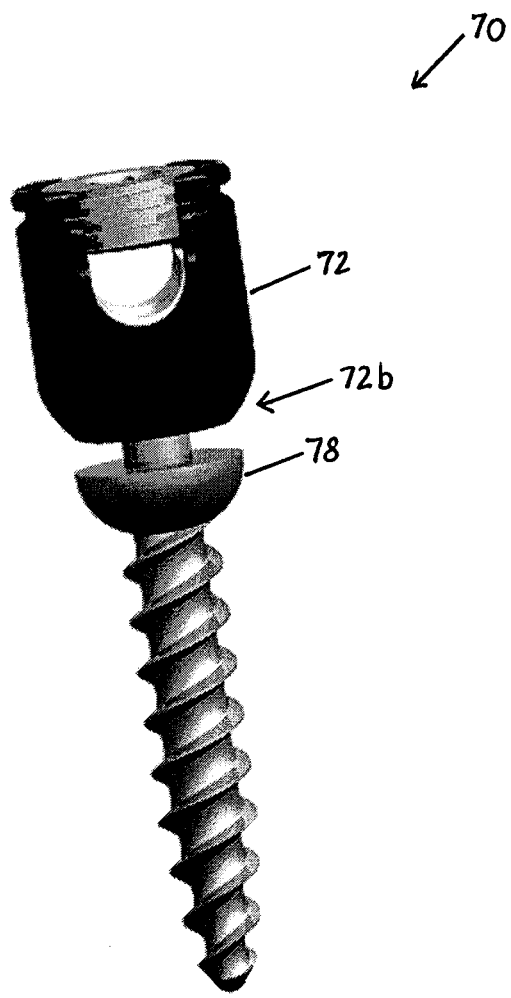
FIG. 7 is a perspective view of another exemplary embodiment of a bone screw including an anti-rotation mechanism in the form of a hemi-spherical member disposed around a proximal portion of a shank of the bone screw.

FIG. 7 illustrates another embodiment of a bone screw 70 having an anti-rotation mechanism 78 disposed distal of a distal end 72b of a receiving head 72 and adapted to engage bone. In this embodiment, the anti-rotation mechanism 78 is in the form of a half dome having a flattened proximal surface and a curved distal surface. While not shown, the dome 78 can include fixation features, such as ridges, spikes, protrusions, serrations, a textured surface, or other features disposed thereon and adapted to engage with bone. In another embodiment, the dome 78 can include a coating, such as hydroxyapatite, disposed thereon and adapted to promote bone ingrowth into the anti-rotation mechanism. In use, the dome 78 can be positioned within a cavity formed by the natural anatomy of the bone, or within a milled cavity as previously discussed above.

Figure 8B:
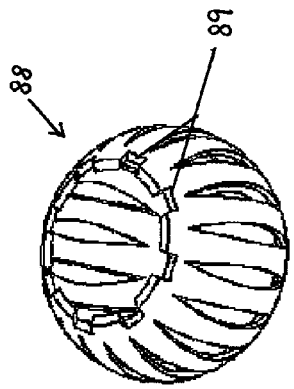
FIG. 8B is a perspective view of the deformable washer of FIG. 8A.
Figure 8C:
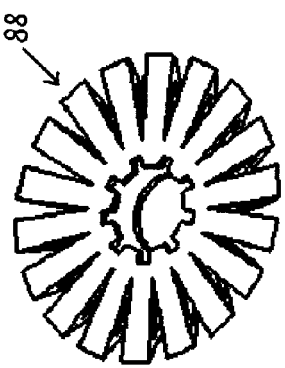
FIG. 8C is a perspective view of the deformable washer of FIG. 8B shown in a deformed configuration.
Figure 8A:
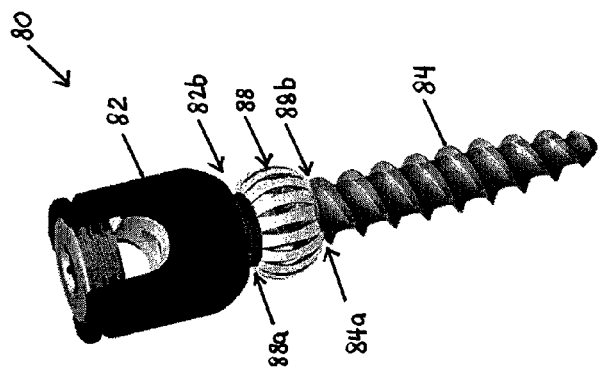
FIG. 8A is a perspective view of another exemplary embodiment of a bone screw having an anti-rotation mechanism in the form of a deformable washer that is adapted to deform and engage bone.

FIGS. 8A-8C illustrate another embodiment of a bone screw 80 having an anti-rotation mechanism that is in the form of a washer 88 disposed between a distal end 82b of the receiving head 82 of the bone screw 80 and around proximal end 84a of the shank 84 of the bone screw 80. The washer 88 can have a variety of configurations, but in the illustrated embodiment it has a generally spherical shape with a plurality of deformable strips extending between proximal and distal ends 88a, 88b thereof. The strips can be formed by formed several longitudinally extending slots in the washer 88. The shape and size of the slots can be optimized to enable the washer 88 to deform in use, as will be discussed below. The washer 88 can also include an inner lumen extending therethrough between the proximal and distal ends 88a, 88b for receiving a proximal portion of the shank 84. The washer 88 can be coupled to the proximal end 84a of the shank 84 using various techniques known in the art. For example, the washer 88 can be threaded onto the shank 84 or it can be integrally attached to the shank 84 during manufacturing. The washer 88 can, however, be mated to or formed on the head 82 of the bone screw 80, or it can be positioned at various other locations on the bone screw 80.

The washer 88 can also include features, such as serrations, surface features, mating notches, teeth, etc., to provide friction between the distal end 82b of the receiver head 82 and the proximal end 88a of the washer 88. By way of non-limiting example, FIG. 8B illustrates serrations 89 formed around the top of the washer 88 for mating with corresponding serrations (not shown) formed around the distal end 82b of the head 82. In use, the friction between the head 82 and washer 88 will help lock the two components together, preventing rotation of the head 82 once the device is implanted.

In use, the washer 88 is adapted to deform and engage bone as the shank 8 is threaded into bone. In particular, as the head 82 is advanced toward a bone surface during insertion of the shank 314 into bone, the washer 88 will be compressed between the head 82 and the bone. The washer 88 will thus deform, as shown in FIG. 8C, to engage bone and thereby prevent the head 82 of the bone screw 80 from rotating relative to the bone. While not shown, the washer 88 can include other fixation features formed thereon to engage bone. For example, the washer 88 can include one or more ridges, spikes, protrusions, serrations, a textured surface, or other features formed thereon for engaging bone as the washer 88 is deformed.

Figure 9A:
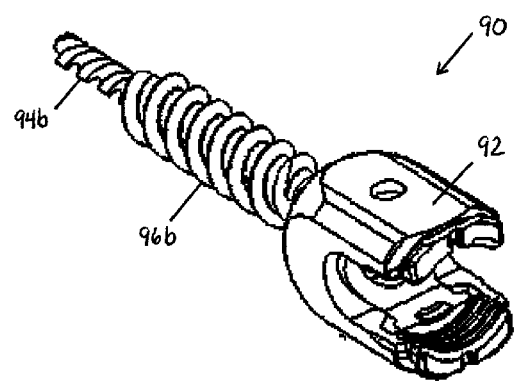
FIG. 9A is perspective view of another exemplary embodiment of a bone screw having an anti-rotation mechanism that is in the form of first and second threaded shanks having threads that extend in opposite directions.
Figure 9B:
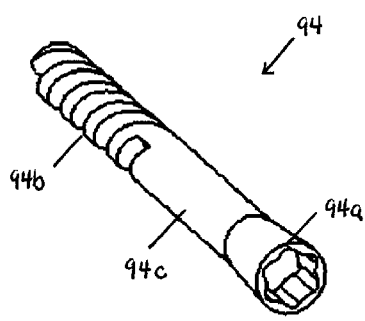
FIG. 9B is a perspective view of one of the first threaded shank of FIG. 9A.
Figure 9C:
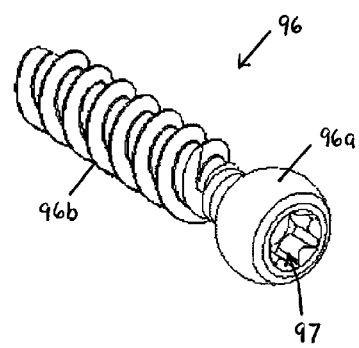
FIG. 9C is a perspective view of one of the second threaded shank of FIG. 9A.

FIGS. 9A-9C illustrate another embodiment of a bone screw 90 having an anti-rotation mechanism for preventing rotation of the head 92 of the bone screw 90 relative to bone. In this embodiment, the shank of the bone screw 90 is formed from first and second threaded portions 94, 96. The first portion 94 has a head 94a and a generally elongate shank 94b extending distally from the head 94a with a first thread disposed therearound. The second portion 96 also has a head 96a and a generally elongate shank 96b extending distally from the head 96a with a second thread disposed therearound. The second portion 96, however, includes an inner lumen 97 extending therethrough for receiving the first portion 94. While not necessary, the shank 94b of the first portion 94 can thus include a non-threaded region 94c that is received within the inner lumen 97 of the second portion 96. As a result, the head 94a of the first portion 94 can sit within the head 96a of the second portion 96 such that the shank 94b of the first portion 94 extends through the shank 96b of the second portion 96. In an exemplary embodiment, the shank 94b of the first portion 94 has a length that is greater than a length of the shank 98b of the second portion 96 to allow the shank 94b of the first portion 94 to extend distally beyond a distal end of the shank 96b of the second portion 96. The thread on the second portion 96 also extends in a direction that is opposite to a direction of the thread on the first portion 94.

In use, the shank 96b of the second portion 96 is threaded into bone by rotating the second portion 96 in a first direction. The head 96a of the second portion 96 can optionally include an internal drive mechanism formed therein for receiving a driver to drive the second portion 96 into bone. When the shank 96b is fully implanted the head 96a will rest against the bone surface. The shank 94b of the first portion 94 is then passed through the shank 96b of the second portion 96 and is threaded into bone by rotating the first portion 94 in an opposite direction. As noted above with respect to the second portion 96, the head 94a of the first portion 96 can likewise optionally include an internal drive mechanism formed therein for receiving a driver to drive the first portion 94 into bone. When the shank 94b is fully implanted, the head 94a of the first portion 94 will reside within the head 96a of the second portion 96, as shown in FIG. 9A. As a result of the opposite-hand threads, the first and second portions 94, 96 will function as an anti-rotation mechanism to prevent rotation of the bone screw 90 relative to bone. The bone screw 90 can also optionally include a locking mechanism for locking the first and second portions 94, 96 together, thereby preventing rotation between the first and second portions 94, 96 once implanted. While various locking techniques can be used, in one embodiment the head 94a of the first portion 94 can be tapered, and the inner lumen 97 of the second portion 96 can have a corresponding tapered portion at its proximal end to allow the two components to engage one another when the first portion 94 is fully inserted through the second portion 96 and is threaded into bone. Other exemplary locking techniques include, by way of non-limiting example, snap rings, an interference fit, biocompatible adhesives, expansion screws, secondary locking caps, etc.

Figure 10A:
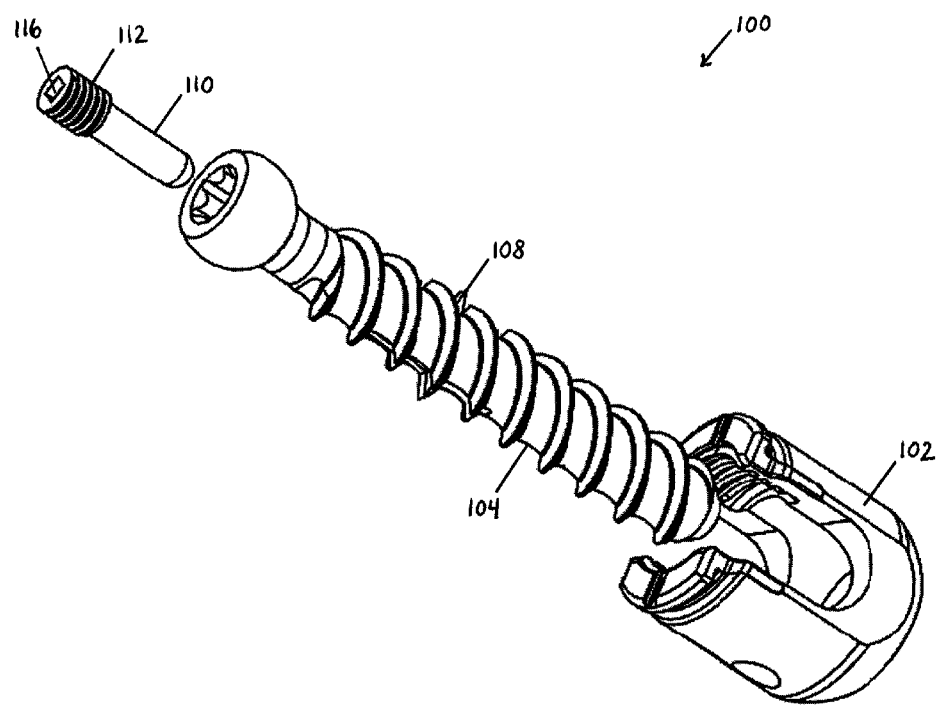
FIG. 10A is an exploded perspective view of another exemplary embodiment of a bone screw having an anti-rotation mechanism in the form of extension members movably coupled to a shank of the bone screw.
Figure 10B:
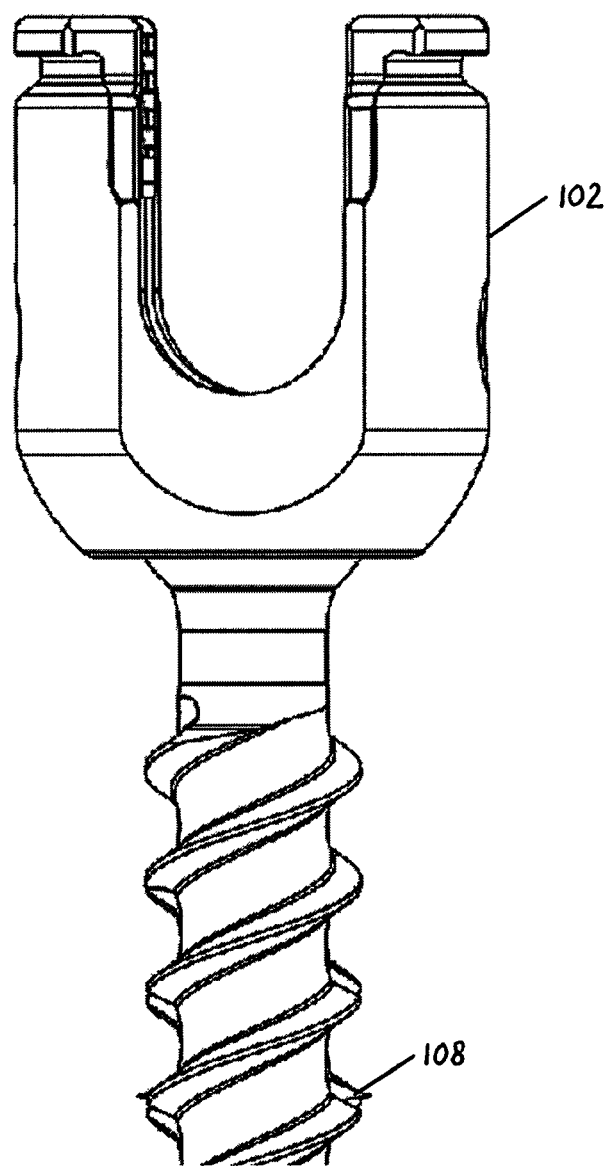
FIG. 10B is a side view of the bone screw of FIG. 10A, showing the extension members in a first retracted position disposed within the shank.
Figure 10C:
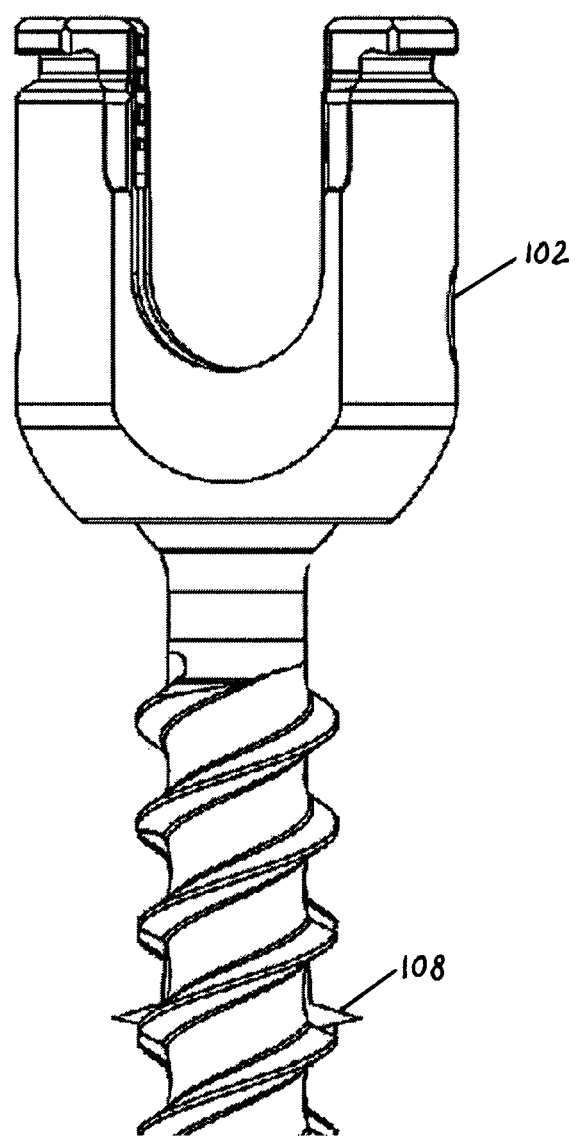
FIG. 10C is a side view of the bone screw of FIG. 10A, showing the extension members in a second extended positioned in which they protrude from the shank to engage bone.
Figure 10D:
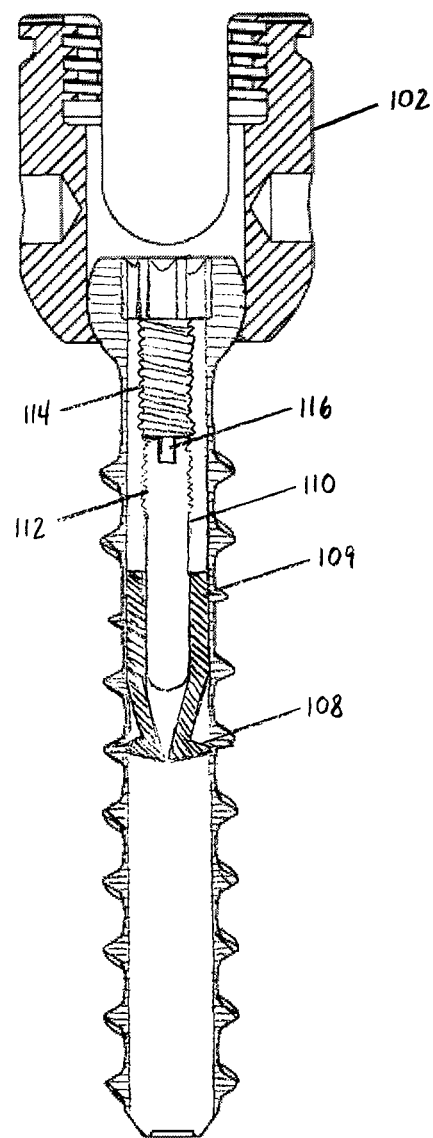
FIG. 10D is a cross-sectional perspective view of the bone screw of FIG. 10A, showing the extension member in a first retraced position disposed within the shank.
Figure 10E:
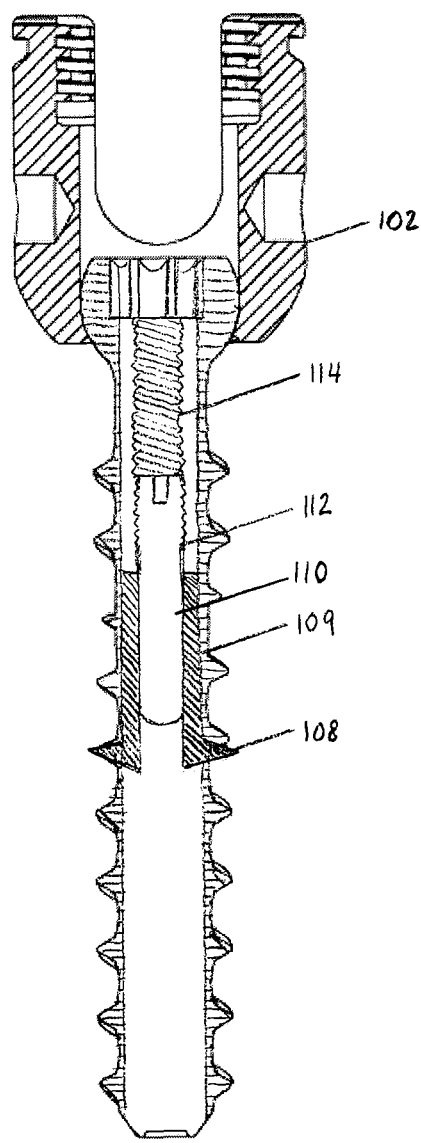
FIG. 10E is a cross-sectional perspective view of the bone screw of FIG. 10A, showing the extension members in a second extended position in which they protrude from the shank to engage bone.
Figure 10F:
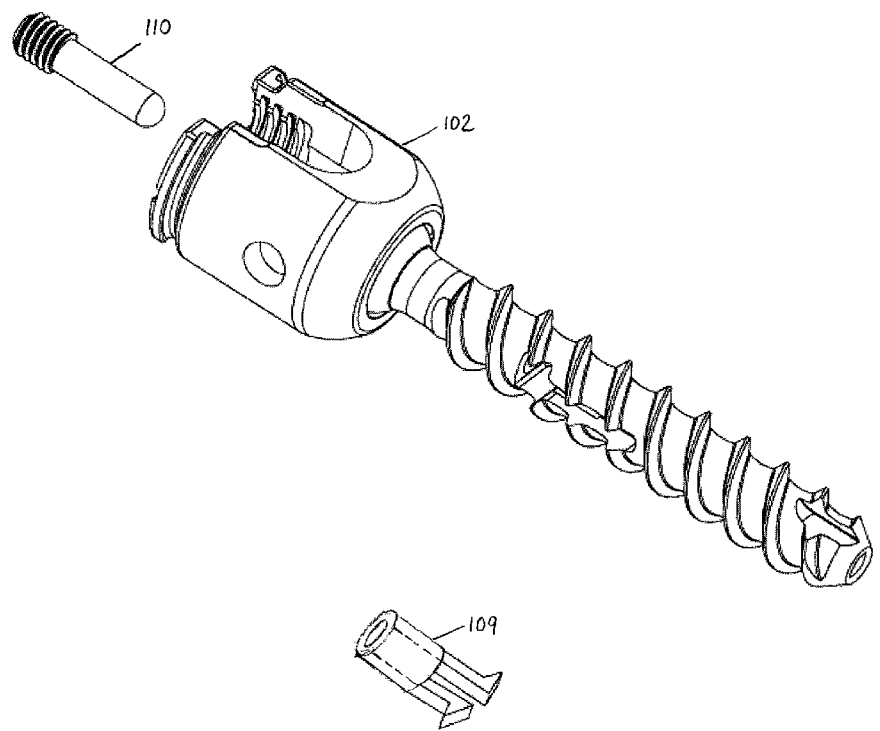
FIG. 10F is an exploded perspective view of the bone screw of FIG. 10A showing a cylindrical body having the extension members extending therefrom.

FIGS. 10A-10F illustrate another exemplary embodiment of a bone screw 100 having an anti-rotation mechanism. In this embodiment, the anti-rotation is in the form of one or more wings or extensions 108 that are disposed within a proximal portion of a shank 104 extending from a head 102 of the bone screw 100, and that are adapted to extend radially outward from the shank 104 to engage bone. The extensions 108 can have a variety of shapes and sizes, but in the illustrated embodiment the extensions 108 are in the form of tapering tabs that extend radially outward from a cylindrical body 109 that is disposed within an inner lumen extending through the shank 104 of the screw 100. The shank 104 can include corresponding openings formed therein for movably receiving the extensions 108 on the body 109. The cylindrical body 109 has an inner lumen extending therethrough and at least the portion of the body 109 containing the extensions 108 is adapted to expand radially outward when a deployment member 110 is received therein. In particular, the body 109 is movable between a first position, shown in FIG. 10D, in which the extensions 108 are at least partially retracted within the shank 104, and a second position, as shown in FIG. 10E, in which the extensions 108 protrude outward from the shank 104 to engage bone. A person skilled in the art will appreciate that the extensions 108 can be sized to seat fully within the shank 104 when the extensions 108 are in a first position so as to avoid interference with insertion of the shank 104 into bone, or they can partially extend from the shank 104 when the extensions 108 are in the first position. Once the shank 104 is implanted in bone, the deployment member 110 can be inserted or advanced through the lumen formed in the body 109 to force the extensions 108 to protrude from the shank 104 and thereby extend into and engage bone surrounding the shank 104 to prevent rotation of the bone screw 100.

The deployment member 110 can have a variety of configurations, but in the illustrated embodiment the deployment member 110 is in the form of an elongate cylindrical member having a distal portion with a diameter that is greater than an inner diameter of the distal portion of the body 109, thus allowing the deployment member 110 to extend the extensions outward from the shank 104 when the deployment member 110 is inserted or advanced into the body 109. Additionally the extensions may be integral to the deployment member and they can be made of a deformable material to extend thru the lumens of the shank 104. The deployment member 110 can have a variety of features to prevent the deployment member 110 from being forced proximally out of the body 109 and allowing the extensions to move from the second position into the first position. For example, the deployment member 110 may have a geometry, locking shoulder recess, or threads to prevent the extensions from forcing the deployment members 110 upward after insertion. In the illustrated embodiment, the deployment member 110 includes threads 112 formed on at least a proximal portion thereof. The inner lumen of the shank 104 includes corresponding threads 114. As the deployment member 110 is advanced into the inner lumen of the shank towards the body 109, the threads 112 are adapted to mate with the threads 114 of the shank 104 to prevent the deployment member 110 from being forced proximally by the extensions 108 when the extensions 108 are in the second deployed position. A person skilled in the art will appreciate that the deployment member 110 can include any features or have any configuration that prevents the deployment member 110 from being forced in the proximal direction when the extensions 108 are in the second position. A variety of techniques can also be used to advance the deployment member 110 into the shank 104 and the body 109. In the illustrated embodiment, a tool can be used to rotate the deployment member 110 into the shank 104 to allow the threads 112 to mate with the threads 114 of the shank 104. For example, a driver having a head with a shape corresponding to the recess 116 formed on the proximal end of the deployment member 110 can be used to removably couple to the deployment member 110 to advance the deployment member 110 into the shank 104 and the body 109. If required, the implant deployment member 110 could be removed, which would retract the extensions allowing the implant to be removed.

The extensions may be integral to the shaft and manufactured from wiring out a spring tab profile. The deployment member 110 would still act to push the extension geometry radially outward.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of fixing a bone screw to bone, comprising:
    implanting a bone anchor into a vertebra, the bone anchor having a receiving head configured for receiving a spinal rod and a shank extending from the receiving head, the receiving head having a substantially rectangular shape such that opposed sidewalls of the receiving head engage adjacent processes of a vertebra to prevent rotation of the receiving head relative to the vertebra; and
    after implanting the bone anchor, seating the spinal rod in the receiving head.

2. A method of fixing a bone screw to bone comprising:
    inserting the bone screw into bone by rotating a shank of the bone screw in a first direction;
    inserting an anti-rotation mechanism through a lumen formed in the shank by rotating the anti-rotation mechanism in a second direction that is opposite to the first direction such that a distal portion of the anti-rotation mechanism engages the bone to thereby prevent rotation of a receiving head of the bone screw relative to the bone;
    positioning a spinal connector within the receiving head of the bone screw; and
    applying a locking mechanism to lock the spinal connector within the receiving head.

3. The method of claim 2, wherein inserting the bone screw into the bone comprises inserting the shank into the bone until a head of the shank rests against a surface of the bone.

4. The method of claim 2, wherein inserting the anti-rotation mechanism comprises inserting the anti-rotation mechanism until the anti-rotation mechanism extends distally beyond a distal-most end of the shank.

5. The method of claim 2, further comprising locking the anti-rotation mechanism and the shank together to prevent rotation of the anti-rotation mechanism relative to the shank.

6. The method of claim 5, wherein the locking comprises engaging a tapered head of the anti-rotation mechanism with a tapered portion of the lumen of the shank.

\* \* \* \* \*